United States Patent [19]

Kamegai et al.

[11] Patent Number: 5,057,311

[45] Date of Patent: Oct. 15, 1991

[54] LOW-IRRITATION DETERGENT COMPOSITION

[75] Inventors: Jun Kamegai, Ichikawa; Hideyuki Hanazawa, Funabashi; Hajime Hirota, Tokyo, all of Japan

[73] Assignee: Kao Corporation, Tokyo, Japan

[21] Appl. No.: 330,278

[22] Filed: Mar. 29, 1989

[30] Foreign Application Priority Data

Apr. 12, 1988 [JP] Japan ................... 63-88291

[51] Int. Cl.⁵ .................. A61K 7/075; A61K 7/50
[52] U.S. Cl. ................................ 424/70; 424/78; 252/174.17; 252/DIG. 13
[58] Field of Search ............. 252/174.17, DIG. 13; 424/70, 78

[56] References Cited

U.S. PATENT DOCUMENTS

| | | | |
|---|---|---|---|
| 3,219,656 | 11/1965 | Boettner | 252/352 X |
| 4,048,301 | 9/1977 | Papantoniou | 424/70 |
| 4,493,773 | 10/1982 | Cook et al. | 252/8.8 |
| 4,663,069 | 5/1987 | Llenzdo | 252/174.117 X |
| 4,678,595 | 7/1987 | Malik | 252/174.17 |
| 4,800,080 | 1/1990 | Grollier et al. | 424/71 X |

FOREIGN PATENT DOCUMENTS 2050166  5/1980  United Kingdom .
2128627  10/1983  United Kingdom .

*Primary Examiner*—Thurman K. Page
*Assistant Examiner*—Susan S. Rucker
*Attorney, Agent, or Firm*—Oblon, Spivak, McClelland, Maier & Neustadt

[57] ABSTRACT

A low-irritation detergent composition comprising (A) an alkyl saccharide-type surface active agent and (B) a cationic polymer. The composition is a low irritant to the skin and hair, produces excellent creamy foam, possesses a superior hair conditioning effect, and imparts an outstanding moisture feeling to the skin.

3 Claims, No Drawings

LOW-IRRITATION DETERGENT COMPOSITION

BACKGROUND OF THE INVENTION

1. Field of the Invention

This invention relates to a low-irritation detergent composition, and, more particularly, to a low-irritation detergent composition comprising an alkyl saccharide-type surface active agent and a cationic polymer. The composition is a low irritant to the skin and hair, produces excellent creamy foam, possesses a superior hair conditioning effect, and imparts an outstanding moisture feeling to the skin.

2. Description of the Backqround

Nonionic surface active agents are widely used in compositions for use in washing the skin and hair. Although nonionic surface active agents possess the advantage of being only slightly irritating, their foaming capability is not sufficient. Because of this, not much of them are formulated into detergent compositions requiring good foaming capability, such as hair shampoos, body shampoos, and the like. Besides the inferior foaming capability and relatively poor detergent capability, which are experienced when a nonionic surface active agent is used alone in a detergent composition, nonionic surface active agents have a problem of imparting a creaky, crinkle feeling to the hair and the skin.

Development of a stable detergent composition comprising a nonionic surface active agent, which is a low irritant to the skin and hair, possesses sufficient foaming and detergent capabilities, and is able to impart a superior feeling the skin, has been desired.

In view of this situation the present inventors have undertaken extensive studies to resolve the above-mentioned problem existing in nonionic surface active agents. As a result, the inventors have found that the combined use of an alkyl saccharide, which is one type of nonionic surface active agent, and a cationic polymer could greatly reduce irritation to the skin and hair, and produce abundant, high quality foam which impart a comfortable slippery feeling to the skin. Such a combined use of an alkyl saccharide and a cationic polymer also provided a detergent composition having an excellent hair conditioning effect and skin moisturizing effect.

SUMMARY OF THE INVENTION

Accordingly, an object of this invention is to provide a low-irritation detergent composition comprising the following components (A) and (B):

(A) at least one alkyl saccharide-type surface active agent represented by formula (I):

$$R_1-O-(R_2O)_m-(G)_n \quad \text{(I)}$$

wherein $R_1$ represents a linear or branched alkyl group of a $C_{8-18}$ carbon atom content, a linear or branched alkenyl group of a $C_{8-18}$ carbon atom content, or an alkylphenyl group of a $C_{8-18}$ carbon atom content, with the alkyl group being either linear or branched, $R_2$ represents an alkylene group of a $C_{2-4}$ carbon atom content, G represents a reduced sugar of a $C_{5-6}$ carbon atom content, m denotes a value of 0 to 10 and n denotes a value of 1 to 10, and (B) at least one cationic polymer.

Other objects, features and advantages of the invention will hereinafter become more readily apparent from the following description.

DETAILED DESCRIPTION OF THE INVENTION AND PREFERRED EMBODIMENTS

As an alkyl saccharide-type surface active agent of formula (I), which is the (A) component of this invention, those having an alkyl group for $R_1$ with 8 to 18, particularly 10 to 14 (decyl group, lauryl group, myristyl group, etc.), carbon atoms are preferable. The value of m in formula (I) is preferably from 0 to 3, with 0 being particularly preferable. The basic unit for the saccharide portion [G in formula (I)], which is the hydrophilic group of the alkyl saccharide-type surface active agent, is a reducing sugar having a $C_{5-6}$ carbon atom content. Glucose, galactose, and fructose are named as examples of desirable reducing sugars. The degree of the polymerization (S) of saccharide, i.e., the value of n in formula (I), is 1 to 10. In particular, use of reducing sugars containing 80% or more of those having the degree of the polymerization (S) of 1 to 4 is desirable. The compounds of formula (I) having a lower degree of the polymerization (S), e.g. 1 to 1.4, are desirable. When the property of the compounds of formula (I) due to the group $R_1$ is taken into account, the value for the polymerization (S) of 1 to 1.4 is desirable for the $R_1$ group with $C_{8-11}$, and (S) of 1.5 to 4.0 is desirable for the $R_1$ group with $C_{12-14}$. The mean values for (S) were determined by proton-NMR method.

Given as specific examples of these alkyl saccharide-type surface active agents are β-alkyl saccharide synthesized by the Koenigs-Knorr method such as octylglucoside, nonylglucoside, decylmaltoside, dodecylmaltoside, tridecylmaltoside, polyoxyethylene (2 E.O.)-dodecylglucoside, and the like; alkyl saccharide produced from a reduced sugar such as glucose, galactose, maltose, or the like and a higher alcohol, polyoxyethylene alkylether glycol, or the like (U.S. Pat. No. 3,219,656, U.S. Pat. No. 3,839,318, and U.S. Pat. No. 4,223,129); and the like.

The (A) component is formulated into the detergent composition of this invention in an amount of 1 to 60% by weight. When the composition is a shampoo, an amount of 5 to 20% by weight is desirable. When it is a composition for use with the skin, an amount of 5 to 50% by weight is desirable.

Enumerated as examples of cationic polymers which can be used in this invention are: cationic cellulose derivatives, cationic starches, copolymers of a diallyl quaternary ammonium salt and an acryl amide, quaternarized polyvinylpyrrolidone derivatives, quaternarized vinylpyrrolidone vinylimidazol polymers (e.g. Luvicuat, manufactured by BASF), polyglycol amine condensates, quaternarized collagen polypeptide, polyethylene imine, cationized silicon polymer [e.g Amodimethicone, described in CTFA; cationic silicon polymers provided in a mixture with other components under the tradename of Dow Corning 929 (cationized emulsion), manufactured by Dow Chemical Co.], copolymers of adipic acid and dimethylaminohydroxypropyl diethylenetriamine (e.g Cartaretine, manufactured by Sandoz Inc.), polyaminopolyamide (e.g. polymers described in French Patent Publication No. 2,252,840 and their crosslinked water-soluble polymers), cationic chitin derivatives, cationized guar gum (e.g. Jaguar C-B-S, Jaguar C-17, Jaguar C-16, etc. manufactured by Celanese Plastics and Specialties Company), quaternary ammonium salt polymers (e.g. Mirapol A-15, Mirapol AD-1, Mirapol AZ-1, etc., manufactured by Miranol Chemical Company Inc., U.S.A.; and polymers described in U.S. Pat. No. 2,261,002, U.S. Pat. No. 2,271,378, U.S. Pat. No. 2,273,780, U.S. Pat. No. 2,388,614, U.S. Pat. No. 2,454,547, U.S. Pat. No. 3,206,462, etc.), as well as cationic polymers selected from groups (a), (b), and (c) below.

(a) A polymer produced by reacting a polyaminopolyamide with epichlorohydrin at an epichlorohydrin mole ratio to the secondary amine group of the polyaminopolyamide of 0.5:1 to 1.8:1. This polyaminopolyam.ide is produced by the reaction of a polyalkylene-polyamine and a dicarboxylic acid selected from the members consisting of saturated fatty acid dicarboxylic acids having a $C_{3-8}$ carbon atom content, and consisting of diglycol acid at a mole ratio of the polyalkylene-polyamine to the dicarboxylic acid of 0.8:1 to 1.4:1. Such a polymer is described in U.S. Pat. No. 3,227,615 and U.S. Pat. No. 2,961,347.

Specifically, this type of polymer is available from Hercules Corp. under the tradename of Hercoset 57. A 10% aqueous solution of this product has a viscosity of 30 cps. In particular, adipic acid epoxypropyl-diethylenetriamine copolymer is provided by Hercules Corp. under the tradename of PD170 or Delsette 101.

(b) A homopolymer or copolymer derived from an acrylic acid or a methacrylic acid having either of the following unit:

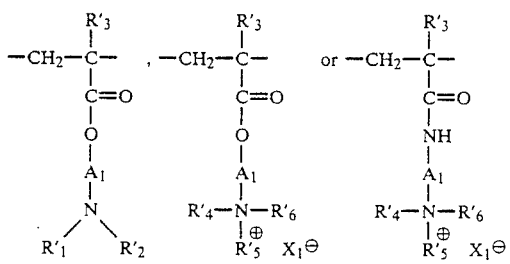

wherein $R'_3$ represents a hydrogen atom or an methyl group, $A_1$ represents a linear or branched alkyl group having a $C_{1-6}$ carbon atom content or a hydroxylalkyl group having a $C_{1-4}$ carbon atom content, $R'_4$, $R'_5$, and $R'_6$, which may be the same or different, represent an alkyl group having a $C_{1-18}$ carbon atom content or a benzyl group, $R'_1$ and $R'_2$ individually represent a hydrogen atom or an alkyl group having a $C_{1-6}$ carbon atom content, and $X_1$ represents a methosulfate anion or a halogen compound such as chloride or bromide.

Copolymers or mixtures of copolymers which can be used are those belonging to the group consisting of acrylamide, methacrylamide, diacetone-acrylamide, acrylamide or methacrylamide with a substituted lower alkyl group for the nirogen atom, alkyl esters of acrylic or methacrylic acid, vinylpyrrolidon, and vinyl esters.

The following copolymers are given as specific examples. Products described in Cosmetic Ingredient Dictionary under the designation of QUATERNIUM 38, 37, 49, or 42; acrylamide/$\beta$-methacryloyloxyethyltrimethylammonium methosulfate copolymers provided by Hercules Corp. under the tradename of Reten 205, 210, 220, or 240; aminoethylacrylate phosphate/acrylate copolymer available from National Starch Co. under the tradename of Catrex, of which an 18% aqueous solution has a viscosity of 700 cps at 25° C.; and cross-linked cationic graft copolymers having a molecular weight of 10,000 to 1,000,000, preferably 15,000 to 500,000, and obtained copolymerizing (i) at least one type of monomer used for cosmetics, (ii) dimethylaminoethyl- methacrylate, (iii) polyethylene glycol, and (iv) poly-unsaturated crosslinking agent. All of the above-mentioned copolymers are described in French Patent No. 2,189,434.

Crosslinking agents which can be used are selected from the group consisting of ethylene glycol dimethacrylate, diallyl phthalate, divinylbenzene, tetraallyl oxyethane, and polyallyl sucrose having 2 to 5 allyl groups per mole of sucrose.

The above-mentioned monomers used for cosmetics encompass a wide variety of monomers. Examples include vinyl esters of an acid having 2 to 18 carbon atoms, allylor methallyl esters of an acid having 2 to 18 carbon atoms, acrylate or methacrylate of a saturated alcohol having 1 to 18 carbon atoms, alkyl vinylether with the alkyl group having 2 to 18 carbon atoms, olefins having 4 to 18 carbon atoms, vinyl-type heterocyclic derivatives, dialkyl- or N,N-dialkylaminoalkyl maleate with the alkyl groups having 1 to 3 carbon atoms, and unsaturated acid anhydrides.

(c) Polymers comprising the units represented by the following formulae (I)' or (II)':

wherein $A_2$ is a group containing 2 amine groups, preferably pyperadinyl groups, and Z represents the symbol B or B', wherein B and B' may be the same or different and represent a linear or branched alkylene group which may be substituted with a hydroxyl- group and may contain one or more oxygen atom, nitrogen atom, sulfur atom, 1 to 3 aromatic groups, and/or heterocyclic ring.

wherein $A_2$ has the same meaning as defined above, and $Z_1$ represents a symbol $B_1$ or $B'_1$, at least one $Z_1$ being the $B'_1$, wherein $B_1$ represents a linear or branched alkylene or hydroxy alkylene group and $B'_1$ represents a linear or branched alkylene group which has at least one nitrogen atom bonded in the chain and may have one or more hydroxyl grou substituents. The nitrogen group has a substituent alkyl group which may have an oxygen atom(s) in the chain and a hydroxyl group substituent(s).

Included also in this group of polymers are cationic polymers selected from quaternary ammonium salts or oxidized products of the above polymers (I)' or (II)'.

Various cationic polymers can be enumerated as mentioned above. Preferable cationic polymers, which can be used as the (B) component of this invention, however, are cationic cellulose derivatives, cationic starches, copolymers of a diallyl quaternary ammonium salt and an acryl amide, quaternarized polyvinylpyrrolidone derivatives, and polyglycol amine condensates.

As a cationic cellulose derivative, a compound which satisfies the following formula (II) is desirable:

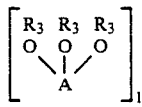 (II)

wherein A indicates a residual group of anhydroglucose units, 1 is an integer of 50 to 20,000, and each $R_3$ indicates a substitution group shown in the following formula (III):

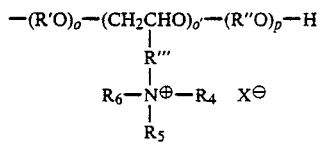 (III)

wherein R' and R" represent alkylene groups having 2 or 3 carbon atoms, o is an integer of 0 to 10, o' is an integer from 0 to 3, p is an integer of 0 to 10, R''' represents an alkylene group or hydroxyalkyl-ene group having 1 to 3 carbon atoms, $R_4$, $R_5$, and $R_6$ may be the same or different, and represent an alkyl, aryl, or aralkyl group having not more than 10 carbon atoms, or may form a heterocyclic ring with a nitrogen atom in the formula, and X designates an anion (chlorine, bromine, iodine, sulfuric acid, sulfonic acid, methyl-sulfuric acid, phosphoric acid, nitric acid, and the like).

The degree of cation substitution of the cationic cellulose, that is, the average value of o' for each anhydroglucose unit is preferably between 0.01 to 1, with the range of 0.02 to 0.5 being more preferable. Also, the total of o+p averages between 1 and 3. A substitution value of smaller than 0.01 is unsatisfactory, while if this value is greater than 1 there is no particular problem, but, from the aspect of reaction yield, a value 1 or smaller is more desirable. The molecular weight of the cationic cellulose used here is in the range of about 100,000 to 3,000,000.

A desirable cationic starch for use in the present invention should satisfy the following formula (IV):

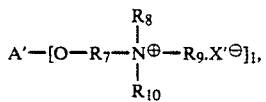 (IV)

wherein A' represents a starch residual group, $R_7$ represents an alkylene group or hydroxyalkylene group, $R_8$, $R_9$, and $R_{10}$ may be the same or different, and represent an alkyl, aryl, or aralkyl group having less than 10 carbon atoms, or may form a heterocyclic ring together with a nitrogen atom in the formula, X' represents an anion (chlorine, bromine, iodine, sulfuric acid, sulfonic acid, methyl-sulfuric acid, phosphoric acid, nitric acid, and the like.), and 1' is a positive integer.

The degree of cation substitution of the cationic starch, i.e., the number of cation groups for each anhydrous glucose group, is desirably 0.01 to 1, with the more desirable range being 0.02 to 0.5 A substitution value of less than 0.01 is unsatisfactory, while if this value is greater than 1 there is no particular problem. However, from the aspect of reaction yield, a value 1 or smaller is more desirable.

A desirable copolymer of a cationic diallyl quaternary ammonium salt and acryl amide for use in the present invention is that which satisfies the following formulae (V) or (VI):

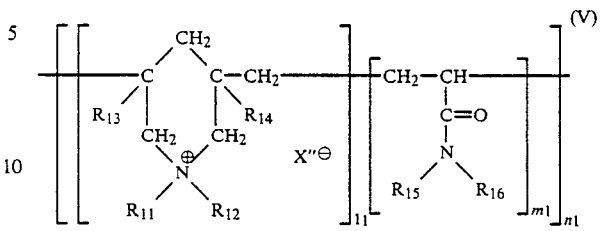

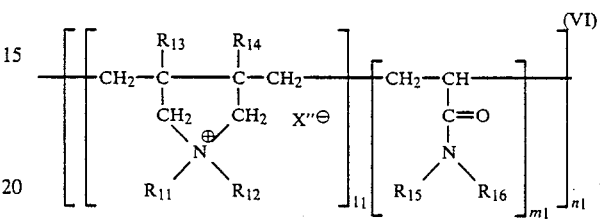

wherein $R_{11}$ and $R_{12}$, which may be the same or different, represent a hydrogen, an alkyl group having 1 to 18 carbon atoms, a phenyl group, an aryl group, a hydroxyalkyl group, an amidoalkyl group, a cyanoalkyl group, an alkoxyalkyl group, or a carboalkoxyalkyl group, $R_{13}$, $R_{14}$, $R_{15}$, and $R_{16}$, which may be the same or different, represent a hydrogen, a lower alkyl group having 1 to 3 carbon atoms, or a phenyl group, X" represents an anion (chlorine, bromine, iodine, sulfuric acid, sulfonic acid, methyl-sulfuric acid, phosphoric acid, nitric acid, or the like.), $l_1$ is an integer of 1 to 50, $m_1$ is an integer of 1 to 50, and $n_1$ is an integer of 150 to 8,000.

The molecular weights of copolymers of diallyl quaternary ammonium salt and acryl amide may be in the range from about 30,000 to 2,000,000, but the range from 100,000 to 1,000,000 is particularly preferable.

A desirable quaternary polyvinylpyrrolidone derivative which can be used in the present invention is represented by the following formula (VII):

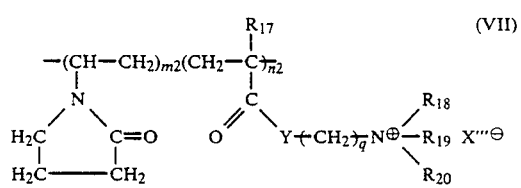 (VII)

wherein $R_{17}$ represents a hydrogen atom or an alkyl group having 1 to 3 carbon atoms, $R_{18}$, $R_{19}$, and $R_{20}$, which may be the same or different, represents a hydrogen atom, an alkyl group, a hydroxyalkyl group, an amidoalkyl group, a cyanoalkyl group, an alkoxyalkyl group, or a carboalkoxyalkyl group, with the alkyl groups having 1 to 4 carbon atoms, Y represents an oxygen atom or an NH group in an amide group, X''' designates an anion (chlorine, bromine, iodine, sulfuric acid, sulfonic acid, alkylsulfuric acid having 1 to 4 carbon atoms, phosphoric acid, nitric acid, and the like.), q is an integer from 1 to 10, and m2 and n2 represent integers satisfying the equation m2+n2=20−8000.

The molecular weights of the quaternary polyvinyl pyrrolidone derivative may be in the range from about 10,000 to 2,000,000, but the range from 50,000 to 1,500,000 is particularly desirable.

The content of the cationic nitrogen derived from the cationic polymer contained in the above-mentioned vinyl polymer is in the range from 0.004% to 0.2% by weight, with the most desirable range being from 0.01% to 0.15% by weight. Below 0.004% the effect is inadequate; above 0.2% the performance is good, but the vinyl polymer becomes colored and the high cost is disadvantageous Given as a desirable polyglycol-polyamine condensate a compound represented by the following formula (VIII):

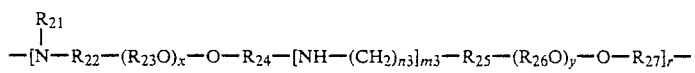

(VIII)

wherein $R_{22}$, $R_{24}$, $R_{25}$, and $R_{27}$ represent hydroxyalkylene groups having 2 to 4 carbon atoms, $R_{23}$ and $R_{26}$ represent alkylene groups having 2 or 3 carbon atoms, x and y represent integers of 10 to 20, m3 represents an integer of 2 to 4, n3 represents an integer of 2 to 6, r represents an integer of 1 to 50, and $R_{21}$ represents a linear or branched alkyl group having 6 to 20 carbon atoms.

One or more of the above-mentioned cationic polymers are used as the (B) component and are formulated into the detergent composition of this invention in an amount of 0.01 to 5% by weight. When the composition is a shampoo the amount of 0.1 to 1.5% by weight is desirable. When it is a composition for use with the skin the amount of 0.01 t 1% by weight is desirable.

It is desirable to adjust the pH of the composition of this invention to 2-10, preferably to 4-8, using an acidic or alkaline pH adjusting agent which is conventionally used in a detergent composition.

Besides the above-mentioned essential components, other components which are generally used in detergent compositions may be optionally formulated into the detergent composition of the present invention inasmuch as the effect of the present invention is not affected. Such components include, for example, humectants such as propylene glycol, glycerin, sorbitol, and the like; viscosity adjusting agents such as carboxyvinyl polymer, methyl cellulose, hydroxyethyl cellulose, polyoxyethyleneglycol distearate, ethanol, and the like; pearling agents; perfumes; pigments; ultraviolet ray absorbers; antioxidants; biocidal agents (Trichlosan, Trichlorocarban, etc.); antiphlogistic agents (potassium glycyl phosphate, tocopherol acetate, etc.); anti-dandruff agents (zinc pyrithione, Octopirox, etc.); antiseptics (methyl paraben, butyl paraben, etc.); and the like.

The detergent composition of this invention can take any conventionally employed preparation forms. The desirable proportion of the components (A) plus (B) in the total amount of the surface active agents in the composition is 30% by weight or greater, when the composition is a solid form, and 10% by weight or greater, when the composition is a liquid form.

Other features of the invention will become apparent in the course of the following description of the exemplary embodiments which are given for illustration of the invention and are not intended to be limiting thereof.

EXAMPLES

Example 1

Shampoos having formulations listed in Table 1 were prepared. Foaming capability and feeling upon touch were evaluated for each shampoo. The results are presented in Table 1.

Evaluation Method

One (1) gm of a shampoo was applied to tresses of hair taken from healthy Japanese women, 15 cm long, weighing 20 gm. The shampoo was lathered for 1 minute, and the foaming conditions were evaluated by 5 expert panelists. Then, the tress was rinsed with tap water for 30 seconds at 30° C., and dried first with a towel, and then with a dryer. The feeling upon touch of the dried hair was evaluated by the same panelists.

Evaluation standard
Foaming capability:
AAA: Lather was abundant
BBB: Lather was normal
CCC: Lather was insufficient
Quality of Lather:
AAA: Lather was creamy
BBB: Lather was rough
Feeling to touch:
AAA: Hair felt soft and not creaky
BBB: Hair was not slippery and felt creaky
BBB: Hair was not slippery and felt creaky

TABLE 1

| | (components: % by weight) | | | | | |
|---|---|---|---|---|---|---|
| | Comparative Product | | Inventive Product | | | |
| | 1 | 2 | 1 | 2 | 3 | 4 |
| $C_{10}$—O—$(G)_{1.5}$*1 | 20 | | 20 | 20 | 20 | 20 |
| $C_{12}$—O—$(G)_{2.0}$*2 | | 20 | | | | |
| Polymer JR-400*3 | | | 0.5 | | | |
| Cationized starch | | | | 0.5 | | |
| Merquat 550*4 | | | | | 0.5 | |
| Gafquat 755*5 | | | | | | 0.5 |
| Purified water | 80 | 80 | 79.5 | 79.5 | 79.5 | 79.5 |
| Evaluation of lather | | | | | | |
| Foaming capability | BBB | BBB | AAA | AAA | AAA | AAA |
| Quality of lather | CCC | CCC | AAA | AAA | AAA | AAA |
| Feeling upon touch | CCC | CCC | AAA | AAA | AAA | AAA |

*1$C_{10}$: decyl group; G: glucose
*2$C_{12}$: dodecyl group; G: glucose
*3A cationized cellulose, manufactured by Union Carbide Corp.
*4A copolymer of N,N-dimethyl-3,5-methylenepyperidinium chloride and acrylamide; manufactured by Merck Co.
*5A triethanolamine salt of ethyl sulfate quarternirized product of vinylpyrrolidone/dimethylaminoethyl acrylate manufactured by Guf Chemical Co.

Example 2

Five percent (5%) aqueous solutions of the detergent compositions of this invention prepared as in Example 1 were subjected to a closed patch test for 24 hours by 5 volunteered panelists. None of the solutions were felt to irritate the skin. Thus, the composition of the invention was proven to be a low irritant.

Example 3

Paste face cleansing foam:
Formulation

| Components | % by weight |
|---|---|
| (1) Alkyl saccharide | 45 |

-continued

| Components | % by weight |
|---|---|
| | [$C_{12}$—O—(G)$_{2.0}$]* | |
| (2) | Cationized cellulose (Polymer JR-400, manufactured by Union Carbide Corp.) | 1 |
| (3) | Ethylene glycol distearate | 3 |
| (4) | Polyethylene glycol 400 | 0.5 |
| (5) | Methyl paraben | 0.2 |
| (6) | Perfume | 0.2 |
| (7) | Purified water | Balance |

*$C_{12}$: dodecyl group; G: glucose

Preparation

To water heated to 70° C. were added components (1) to (5) under stirring to obtain a transparent solution. After cooling this solution to 40° C., component (6) was added and the mixture was cooled to the room temperature.

The pasty face cleansing foam containing an alkyl saccharide-type surface active agent and a cationized cellulose thus prepared prdouced abundant lather, was able to be readily rinsed away, and provided a comfortable moistening feeling after cleansing. In addition, the face cleansing foam had a superior low-temperature stability.

Example 4

Shampoo composition
Formulation

| Components | % by weight |
|---|---|
| (1) | Alkyl saccharide [$C_{10}$—O—(G)$_{1.5}$]*$^1$ | 20 |
| (2) | Merquat 550*$^2$ | 0.3 |
| (3) | Polyethylene glycol distearate*$^3$ | 1 |
| (4) | Methyl paraben | 0.2 |
| (5) | Blue #1 | Small amount |
| (6) | Perfume | 0.2 |
| (7) | Purified water | Balance |

*$^1$$C_{10}$: decyl group; G: glucose
*$^2$A copolymer of N,N-dimethyl-3,5-methylenepyperidinium chloride and acrylamide; manufactured by Merck Co.
*$^3$Emanone 3299 manufactured by Kao Corp.

Preparation

To purified water heated to 60° C. were added components (1) to (5) under stirring to obtain a transparent solution. After cooling this solution to 40° C., component (6) was added and the mixture was cooled to room temperature.

The shampoo composition containing an alkyl saccharide-type surface active agent and a cationizaed polymer thus prepared produced abundant lather, was able to be readily rinsed away, and provided a comfortable moistening feeling to the hair after shampooing. In addition, the shampoo composition had a superior low-temperature stability.

Example 5

Shampoo composition
Formulation

| Components | % by weight |
|---|---|
| (1) | Alkyl saccharide [$C_{10}$—O—(G)$_{1.4}$]*$^1$ | 10 |
| (2) | Gafquat 755*$^2$ | 0.4 |
| (3) | Sodium polyoxyethylene(2)-lauryl sulfate | 5 |
| (4) | Coconut oil diethanolamide | 1 |

-continued

| Components | % by weight |
|---|---|
| (5) | Sodium chloride | 1 |
| (6) | Perfume | 0.2 |
| (7) | Purified water | Balance |

*$^1$$C_{10}$: decyl group; G: glucose
*$^2$A ethyl sulfate quarternirized triethanolamine of vinylpyrrolidone/dimethylaminoethyl acrylate manufactured by Gaf Chemical Co.

To purified water heated to 60° C. were added components (1) to (5) under stirring to obtain a transparent solution. After cooling this solution to 40° C., component (6) was added and the mixture was cooled to room temperature.

The shampoo composition containing alkyl saccharide-type surface active agent and a cationized polymer thus prepared produced abundant lather, was readily rinsed away, and provided a comfortable moistening feeling to the hair after shampooing. In addition, the shampoo composition had a superior low-temperature stability.

Example 6

Anti-dandruff shampoo
Formulation

| Components | % by weight |
|---|---|
| (1) | Alkyl saccharide [$C_{12}$—O—(G)$_{1.7}$]* | 15 |
| (2) | Cationized cellulose (Polymer JR-400, manufactured by Union Carbide Corp.) | 0.2 |
| (3) | Tomicide Z-50 (Zinc pyrithion, manufactured by Yoshitomi Pharmaceutical Ind. | 1 |
| (4) | Methyl paraben | 0.1 |
| (5) | Perfume | 0.2 |
| (6) | Purified water | Balance |

*$C_{12}$: lauryl group; G: glucose

To purified water heated to 60° C. were added components (1) to (4) under stirring to obtain a transparent solution. After cooling this solution to 40° C., component (5) was added and the mixture was cooled to room temperature.

The anti-dandruff shampoo containing alkyl saccharide-type surface active agent and a cationized polymer thus prepared produced abundant lather, was readily rinsed away, and provided a comfortable moistening feeling to the hair after shampooing. In addition, the shampoo composition had a superior low-temperature stability.

Example 7

Liquid face cleansing form
Formulation

| Components | % by weight |
|---|---|
| (1) | Alkyl saccharide [$C_{12}$—O—(G)$_{1.7}$]* | 35 |
| (2) | Cationized cellulose (Polymer JR-400, manufactured by Union Carbide Corp.) | 1 |
| (3) | Ethylene glycol distearate | 3 |
| (4) | Triethanolamine laurate | 5 |
| (5) | Methyl paraben | 0.2 |
| (6) | Ethanol | 4 |
| (7) | Perfume | 0.2 |

| Components | % by weight |
| --- | --- |
| (8) Purified water | Balance |

*$C_{12}$: lauryl group; G: glucose

To purified water heated to 70° C. were added components (1) to (5) under stirring to obtain a transparent solution. After cooling this solution to 50° C., component (6) was added and the mixture was cooled to room temperature. Component (7) was then added to the mixture.

The liquid face creansing form containing alkyl saccharide-type surface active agent and a cationized polymer thus prpeared produced abundant lather, was readily rinsed away, and provided a comfortable moistening feeling to the skin after creansing. In addition, the liquid face creansing form had a superior low-temperature stability.

Example 8

Body shampoo
Formulation

| Components | % by weight |
| --- | --- |
| (1) Alkyl saccharide $[C_{12}-O-(G)_{1.7}]$*1 | 30 |
| (2) Merquat 550*2 | 0.1 |
| (3) Ethylene glycol distearate | 3 |
| (4) Hydroxyethyl cellulose | 0.2 |
| (5) Irgasan DP-300 (Triclosan, manufactured by Ciba Geigy) | 0.5 |
| (6) Ethanol | 5 |
| (7) Methyl paraben | 0.2 |
| (8) Perfume | 0.2 |
| (9) Purified water | Balance |

*1$C_{12}$: lauryl group; G: glucose
*2A copolymer of N,N-dimethyl-3-5-methylenepyperidinium chloride and acrylamide; manufactured by Merck Co.

To purified water heated to 70° C. were added components (1) to (7) under stirring to obtain a transparent solution. After coolnig ths solution to 40° C., component (8) was added and the mixture was cooled to room temperature.

The body shampoo containing alkyl saccharide-type surface active agent and a cationized polymer thus prepared produced abundant lather, was readily rinsed away, and provided a comfortable moistening feeling to the skin after shampooing. In addition, the body shampoo had a superior low-temperature stability.

Example 9

Shampoo composition
Formulation

| Components | % by weight |
| --- | --- |
| (1) Alkyl saccharide $[C_8-O-(G)_{1.3}]$*1 | 20 |
| (2) Jaguar C-13-S*2 | 0.5 |
| (3) Octopirox | 0.5 |
| (4) Disodium ethylenediamine tetraacetate | 0.4 |
| (5) Perfume | 0.6 |
| (6) Ethanol | 5 |
| (7) Purified water | Balance |

*1$C_8$: octyl group; G: glucose
*2Quaternarized guar gum, manufactured by Celanese Co.

To purified water heated to 60° C. were added components (1) to (4) under stirring. Component (6) was added to the solution which was cooled to 55° C. After cooling this solution to 40° C., component (5) was added and the mixture was cooled to room temperature.

The shampoo composition containing alkyl saccharide-type surface active agent and a cationized polymer thus prepared produced abundant lather, was readily rinsed away, and provided a comfortable moistening feeling to the hair after shampooing.

Example 10

Shampoo composition
Formulation

| Components | % by weight |
| --- | --- |
| (1) Alkyl saccharide $[C_{12}-O-(CH_2CH_2O)_2-G]$*1 | 18 |
| (2) Jaguar C-13*2 | 0.5 |
| (3) Laurylamineoxide | 2.0 |
| (4) Perfume | 0.5 |
| (5) Purified water | Balance |

*1$C_{12}$: lauryl group; G: glucose
*2Cationized guar gum manufactured by Celanese Co.

To purified water heated to 70° C. were added components (1) to (3) under stirring. Component (4) was added to the solution which was cooled to 50° C. This solution was cooled to room temperature to obtain the target shampoo composition.

The shampoo composition containing alkyl saccharide-type surface active agent and a cationized polymer thus prepared produced abundant lather, was readily rinsed away, and provided a comfortable moistening feeling to the hair after shampooing.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent is:

1. A low-irritation detergent composition consisting essentially of the following components (A), (B) and (C):

(A) at least one alkyl saccharide surface active agent represented by formula (I):

$$R_1-O-(R_2O)_m-(G)_n \qquad (I)$$

wherein $R_1$ represents a linear or branched alkyl group of a $C_{8-18}$ carbon atom content, a linear or branched alkenyl group of a $C_{8-18}$ carbon atom content, or an alkylphenyl group of a $C_{8-18}$ carbonm atom content, with the alkyl group being either linear or branched, $R_2$ represents an alkylene group of a $C_{2-4}$ carbon atom content, G represents a reduced sugar of a $C_{5-6}$ carbon atom content, m denotes a value of 0 to 10 and n denotes a value of 1 to 10, (B) at least one cationic poylmer and (C) at least one humectants, pearling agents, perfumes, pigments, ultraviolet ray absorbers, antioxidants, biocidal agents, antiphlogistic agents, antidandruff agents, antiseptics, and synthetic surfactants other than alkyl saccharide surfactants.

2. A low-irritation detergent composition consisting essentially of the following components (A), (B) and (C):

(A) at least one alkyl saccharide surface active agent represented by formula (I):

$$R_1-O-(R_2O)_m-(G)_n \qquad (I)$$

wherein $R_1$ represents a linear or branched alkyl group of a $C_{8-18}$ carbon atom content, a linear or branched alkenyl group of a $C_{8-18}$ carbon atom content, or an alkylphenyl group of a $C_{8-18}$ carbon atom content, with the alkyl group being either linear or branched, $R_2$ represents an alkylene group of a $C_{2-4}$ carbon atom content, G represents a reduced sugar of a $C_{2-4}$ carbon atom content, m denotes a value of 0 to 10 and n denotes a value of 1 to 10, (B) at least one cationic polymer and (C) at least one humectants, pearling agents, perfumes, pigments, ultraviolet ray absorbers, antioxidants, biocidal agents, antiphlogistic agents, antidandruff agents, antiseptics, sodium polyoxyethylene (2)-lanoyl sulfate and triethanolamine laurate.

3. A low-irritation detergent composition according to claim 1 or 2, wherein said cationic polymer is at least one member selected from the group consisting of cationic cellulose derivatives, cationic starches, copolymers of a diallyl quaternary ammonium salt and an acryl amide, quaternarized polyvinylpyrrolidone derivatives, and polglycol amine condensates.

* * * * *